(12) United States Patent
Henrion et al.

(10) Patent No.: US 6,492,502 B2
(45) Date of Patent: Dec. 10, 2002

(54) AZO COMPOUNDS, USE IN DYEING, COMPOSITIONS CONTAINING THEM AND DYEING PROCESSES

(75) Inventors: Jean-Christophe Henrion, Pantin; Michel Philippe, Wissous, both of (FR)

(73) Assignee: L'Oreal, S.A., Paris (FR)

( * ) Notice: Subject to any disclaimer, the term of this patent is extended or adjusted under 35 U.S.C. 154(b) by 35 days.

(21) Appl. No.: 09/737,847

(22) Filed: Dec. 18, 2000

(65) Prior Publication Data

US 2001/0001332 A1 May 24, 2001

Related U.S. Application Data

(62) Division of application No. 09/197,462, filed on Nov. 23, 1998, now Pat. No. 6,179,881.

(30) Foreign Application Priority Data

Nov. 21, 1997 (FR) .............................................. 97 14658

(51) Int. Cl.$^7$ ............................................. C07C 245/06
(52) U.S. Cl. ........................ 534/738; 534/770; 534/885
(58) Field of Search ................. 534/738, 770, 534/885

(56) References Cited

U.S. PATENT DOCUMENTS

| | | | |
|---|---|---|---|
| 2,185,154 A | 12/1939 | Lecher et al. | |
| 2,369,309 A | 2/1945 | McClellan et al. | |
| 3,861,868 A | 1/1975 | Milbrada | |
| 4,731,383 A | * 3/1988 | Erczi et al. | 514/634 |
| 4,886,517 A | 12/1989 | Bugaut et al. | |

FOREIGN PATENT DOCUMENTS

| | | |
|---|---|---|
| CS | 441310 | 1/1968 |
| DE | 2 816 350 | 10/1978 |
| EP | 325936 | 8/1989 |
| FR | 2 132 214 | 11/1972 |
| FR | 2 570 946 | 4/1986 |
| FR | 2 586 913 | 3/1987 |

OTHER PUBLICATIONS

Dr. Siegfried Petersen et al., "Synthese einfacher Chinon–Derivate mit fungiziden, bakteriostatischen oder cytostatischen Eignschaften," Angewandte Chemie, vol. 67, No. 8, 1955, pp. 217–231.

English Language Derwent Abstract of DE 2 816 350.
English Language Derwent Abstract of FR 2 586913.

* cited by examiner

Primary Examiner—Fiona T. Powers
(74) Attorney, Agent, or Firm—Finnegan, Henderson, Farabow, Garrett & Dunner, L.L.P.

(57) ABSTRACT

Azo compounds of the 2-(4-amino) phenyldiazinecarboximidamide type and 2-(4-amino) phenylhydrazinecarboximidamide type, a process for their synthesis, their use for dyeing keratin fibers, dye compositions containing them, and dyeing processes.

10 Claims, No Drawings

AZO COMPOUNDS, USE IN DYEING, COMPOSITIONS CONTAINING THEM AND DYEING PROCESSES

This is a division of application Ser. No. 09/197,462, filed Nov. 23, 1998, now U.S. Pat. No. 6,179,881 which is incorporated herein by reference.

The present invention relates to novel azo compounds of the 2-(4-amino)phenyidiazinecarboximidamide type, to a process for their synthesis, to their use for dyeing keratin fibers, to dye compositions containing them and to dyeing processes using them.

It is well known that hair dye compositions use either oxidation dyes or direct dyes. The former dyes lead to shades with better covering power and better staying power, but they have the disadvantage of not being entirely harmless and of requiring an oxidation which is generally accompanied by appreciable degradation of the keratin fibers. In addition, their staying power and their affinity for the hair usually entails the appearance of the phenomenon of demarcation between dyed ends and half-lengths and undyed roots.

These problems do not arise in the case of direct dyes. The use of direct dyes has the further advantage over oxidation dye precursors of reducing the potential risks of allergy.

Among the direct dyes most commonly used are nitrobenzene derivatives. However, these nitrobenzene dyes do not sufficiently withstand repeated washing. To overcome this flaw, attempts have been made to replace nitrobenzene dyes with aminoanthraquinone dyes or azo dyes. It has already been proposed, in particular in patent application FR-A-2,570,946, to use the azo dye of the following formula:

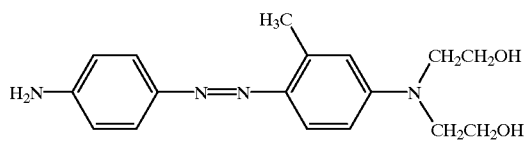

i.e. 4-amino-2'-methyl-4'-[N,N-bis(b-hydroxyethyl)amino] phenylazobenzene.

However, the use of this compound to dye the hair does not yield entirely satisfactory results, in particular, regarding the intensity of the colourings obtained.

The inventors have thus sought other azo dyes which have good solubility in a medium suitable for dyeing, such as water, water/alcohol mixtures and more generally common dye supports and which give, on keratin fibers, dyes with good resistance properties with respect to the various attacking factors to which keratin fibers may be subjected, and in particular with respect to washing, light, bad weather and perspiration.

Thus, following these investigations, the inventors have discovered azo compounds of the 2-(4-amino) phenyidiazinecarboximidamide type of formula (I) defined below.

This discovery forms the basis of the present invention.

The present invention is thus novel azo compounds of formula (I) below, and acid addition salts thereof:

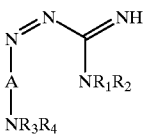

(I)

in which:

R$_1$ and R$_2$, independently of each other, represent a hydrogen atom; a C$_1$–C$_6$ alkyl radical; a 5- or 6-membered cycloalkyl radical; a 5- or 6-membered aromatic ring; a 5- or 6-membered aromatic ring substituted with a C$_1$–C$_6$ alkyl radical, a halogen atom, an amino radical, a hydroxyl radical or a C$_1$–C$_6$ alkoxy radical; or R$_1$ and R$_2$ form, together with the nitrogen atom to which they are attached, a 4- to 8-membered heterocycle, said heterocycle containing one or more hetero atoms chosen from sulfur, nitrogen and oxygen;

R$_3$ and R$_4$, independently of each other, represent a hydrogen atom, a C$_1$–C$_6$ alkyl radical, a C$_1$–C$_6$ monohydroxyalkyl radical or a C$_2$–C$_5$ polyhydroxyalkyl radical; and A is a 5- to 6-membered aromatic ring which can be interrupted by one or more hetero atoms chosen from sulfur, nitrogen and oxygen, or fused to another 5- to 6-membered aromatic ring.

When used to dye keratin fibers, the compounds of formula (I) in accordance with the invention have good solubility in water, in water/alcohol mixtures and more generally in common dye supports, and give colourings in a very intense coppery-orange shade which are particularly resistant to the various treatments to which the fibers may be subjected, such as washing, light, bad weather and perspiration. The coppery-orange colourings obtained using the compounds of formula (I) in accordance with the invention are, in particular, more intense than those obtained under the same conditions with 4-amino-2'-methyl-4'-[N,N'-bis(b-hydroxyethyl)amino]phenylazobenzene mentioned above.

In formula (I) above, the alkyl, monohydroxyalkyl and polyhydroxyalkyl radicals may be linear or branched.

Among the C$_1$–C$_6$ alkyl radicals of the compounds of formula (I) above, preferred alkyl radicals are: methyl, ethyl, n-propyl, isopropyl, n-butyl, isobutyl, tert-butyl, n-pentyl, isopentyl, n-hexyl and isohexyl radicals.

Among the C$_1$–C$_6$ monohydroxyalkyl radicals, preferred monohydroxyl radicals are: hydroxymethyl, hydroxyethyl, hydroxypropyl and hydroxybutyl radicals.

Among the C$_2$–C$_6$ polyhydroxyalkyl radicals, preferred polyhydroxylalkyl radicals are: dihydroxyethyl, dihydroxypropyl, trihydroxypropyl and dihydroxybutyl radicals.

Among the cycloalkyl radicals which can be represented by the radicals R$_1$ and R$_2$, preferred cycloalkyl radicals are: cyclohexyl and cyclopentyl.

Among the aromatic rings which can be represented by the radicals R$_1$ and R$_2$, preferred aromatic rings are, for example, phenyl rings; phenyl rings substituted with a C$_1$–C$_6$ alkyl radical, a halogen atom or an amino, hydroxyl or C$_1$–C$_6$ alkoxy radical; benzyl, pyrimidine, pyridazine and benzimidazole rings.

Among the heterocycles which can be formed by the radicals R$_1$ and R$_2$ together, preferred heterocycles are: imidazole, benzotriazole, benzimidazole, pyrrolidine, piperidine and morpholine rings.

Among the rings which can be represented by the aromatic ring A, preferred rings are, for example, 6-membered rings such as phenyl, pyrimidine and pyridine rings, and 5-membered rings such as pyrrole and pyrazole rings.

The radicals $R_1$, $R_2$, $R_3$ and $R_4$, independently of each other, preferably represent a hydrogen atom or a methyl radical.

Among the compounds of formula (I), mention may be made in particular of:

2-(4-amino)phenyldiazinecarboximidamide,
N,N-dimethyl-2-(4-amino)phenyldiazinecarboximidamide,
N,N-diethyl-2-(4-amino)phenyldiazinecarboximidamide,
N,N-diisopropyl-2-(4-amino)phenyldiazinecarboximidamide,
N,N-dibutyl-2-(4-amino)phenyldiazinecarboximidamide,
2-(5-amino)-2-pyridyldiazinecarboximidamide,
and the acid addition salts thereof.

The compounds of formula (I) in accordance with the invention can readily be obtained, according to methods well known in the state of the art, which comprise, in a first step, carrying out, in a solvent medium, a reduction reaction on a compound of formula (III) below:

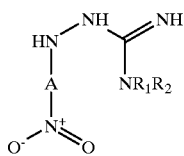
(III)

in which A, $R_1$ and $R_2$ can take the same meanings as those indicated above for the compounds of formula (I), to give a compound of 2-(4-amino)phenylhydrazinecarboximidamide type of formula (II) below:

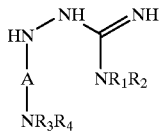
(II)

in which A, $R_1$, $R_2$, $R_3$ and $R_4$ have the same meanings as those indicated above for the compounds of formula (I), which product, in a second step, is oxidized, in a solvent medium, to give the corresponding compound of formula (I).

According to a variant of this synthetic process, and when, in the compounds of formula (I), at least one of the radicals $R_3$ and $R_4$ is other than a hydrogen atom, the process then includes an intermediate step of substituting the amine according to the known standard methods.

When the synthesis is complete, the compounds of formula (I) in accordance with the invention can, where appropriate, be recovered by methods which are well known in the state of the art, such as crystallization or distillation.

The solvent(s) used in steps 1 and 2 above is (are) preferably chosen from water, $C_1$–$C_4$ alkanols such as methanol, ethanol or isopropanol, and mixtures thereof.

The reduction reaction used in the first step is preferably a catalytic hydrogenation, the catalyst being, for example, palladium on charcoal.

The oxidizing agents which can be used in the second step are preferably chosen from sodium iodate, sodium periodate, atmospheric oxygen, magnesium phthalate monoperoxide, hydrogen peroxide and hydrogen peroxide in the presence of metal salts such as, for example, manganese diacetate, potassium ferricyanide, silver oxide and ferric chloride.

The pH of the synthetic medium used in the first and second steps is not a critical factor, and preferably ranges from approximately 4 to 10. It can be adjusted using basifying or acidifying agents which are well known in the state of the art.

The temperature of the reactions carried out in steps 1 and 2 generally ranges from approximately 0 to 60° C.

Another aspect of the invention is the use of the compounds of formula (I) in accordance with the invention as dyes for dyeing keratin fibers, and in particular human keratin fibers such as the hair.

The intermediate compounds of formula (II) above can also be used as dyes, and in particular as auto-oxidizing dyes (i.e. dyes which do not require the use of an oxidizing agent in order to give a colouring) for dyeing keratin fibers, in particular human keratin fibers such as the hair.

Among the compounds of formula (II), preferred compounds are:

2-(4-amino)phenylhydrazinecarboximidamide,
N,N-dimethyl-2-(4-amino)phenylhydrazinecarboximidamide,
N,N-diethyl-2-(4-amino)phenylhydrazinecarboximidamide,
N,N-diisopropyl-2-(4-amino)phenylhydrazinecarboximidamide,
N,N-dibutyl-2-(4-amino)phenylhydrazinecarboximidamide,
2-(5-amino)-2-pyridylhydrazinecarboximidamide,
and the acid addition salts thereof.

Certain compounds of formula (II) above are novel per se and, in this respect, constitute another aspect of the invention. These novel compounds, and the acid addition salts thereof, correspond to formula (II') below:

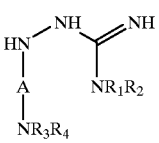
(II')

in which A, $R_1$, $R_2$, $R_3$ and $R_4$ have the same meanings as those indicated above for the compounds of formula (I), with the proviso that at least one of the radicals $R_1$, $R_2$, $R_3$ and $R_4$ is other than a hydrogen atom.

2-(4-Amino)phenylhydrazinecarboximidamide (compound of formula (II') in which $R_1$, $R_2$, $R_3$ and $R_4$ simultaneously represent a hydrogen atom) is mentioned in an article by Petersen S. et al. (Angew. Chem., 67(1955), pages 217–231) with regard to quinone-based fungicides.

Among the compounds of formula (II') in accordance with the invention, preferred compounds are:

N,N-dimethyl-2-(4-amino)phenylhydrazinecarboximidamide,
N,N-diethyl-2-(4-amino)phenylhydrazinecarboximidamide,
N,N-diisopropyl-2-(4-amino)phenylhydrazinecarboximidamide,
N,N-dibutyl-2-(4-amino)phenylhydrazinecarboximidamide,
2-(5-amino)-2-pyridylhydrazinecarboximidamide,
and the acid addition salts thereof.

Yet another aspect of the invention is a composition for dyeing keratin fibers, and in particular human keratin fibers such as the hair, that comprises, in a medium which is suitable for dyeing, at least one compound of formula (I) in accordance with the invention and/or at least one compound of formula (II) in accordance with the invention.

The compound(s) of formula (I) and/or the compound(s) of formula (II) preferably represent(s) from 0.0005 to 12% by weight approximately relative to the total weight of the dye composition, and even more preferably from 0.005 to 6% by weight approximately relative to this weight.

The medium suitable for dyeing, such as water, water/alcohol mixtures and more generally common dye supports generally comprises water or a mixture of water and at least one organic solvent to dissolve any compounds which are not sufficiently water-soluble. Preferred organic solvents are, for example, $C_1$–$C_4$ lower alkanols, such as ethanol and isopropanol; glycerol; glycols and glycol ethers such as 2-butoxyethanol, propylene glycol, propylene glycol monomethyl ether and diethylene glycol monoethyl ether and monomethyl ether, as well as aromatic alcohols such as benzylalcohol or phenoxyethanol, similar products and mixtures thereof.

The solvents can be present in proportions preferably ranging from 1 to 40% by weight approximately relative to the total weight of the dye composition, and even more preferably from 5 to 30% by weight approximately.

The pH of the dye composition in accordance with the invention generally ranges from approximately 3 to 12, and preferably approximately from 5 to 11. It can be adjusted to the desired value using acidifying or basifying agents usually used to dye keratin fibers.

Preferred acidifying agents include, for example, inorganic or organic acids such as hydrochloric acid, orthophosphoric acid, sulfuric acid, carboxylic acids such as acetic acid, tartaric acid, citric acid and lactic acid, and sulfonic acids.

Preferred basifying agents are, for example, aqueous ammonia, alkaline carbonates, alkanolamines such as mono-, di- and triethanolamines and derivatives thereof, sodium hydroxide, potassium hydroxide and the compounds of formula (IV) below:

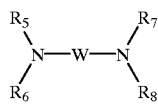

(IV)

in which W is a propylene residue optionally substituted with a hydroxyl radical or a $C_1$–$C_6$ alkyl radical; $R_5$, $R_6$, $R_7$ and $R_8$, which may be identical or different, represent a hydrogen atom, a $C_1$–$C_6$ alkyl radical or a $C_1$–$C_6$ hydroxyalkyl radical.

The dye composition in accordance with the invention can also contain various adjuvants conventionally used in hairdye compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, modified or unmodified, volatile or non-volatile silicones, film-forming agents, ceramides, preserving agents and opacifiers.

Needless to say, a person skilled in the art can select optional complementary compounds such that the advantageous properties intrinsically associated with the dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibers, and in particular human hair.

In particular, to facilitate the oxidation of the compounds of formula (II) in accordance with the invention, when oxidizing agents are present in the dye composition or when the composition contains at least one oxidation dye precursor, the said composition can also contain one or more oxidizing agents. These oxidizing agents can be chosen, in particular, from hydrogen peroxide, urea peroxide, alkali metal bromates, persalts such as perborates and persulfates, and enzymes such as peroxidases and two-electron oxidoreductases. It is particularly preferred to use hydrogen peroxide or enzymes.

As has been mentioned above, the dye composition in accordance with the invention can also contain one or more oxidation dye precursors, i.e. one or more oxidation bases and/or one or more couplers. The oxidation bases can be chosen in particular from para-phenylenediamines, para-aminophenols, orthophenylenediamines and heterocyclic bases such as, for example, pyridine derivatives, pyrimidine derivatives, pyrazole derivatives and pyrazolopyrimidine derivatives. The couplers can be chosen in particular from meta-phenylenediamines, meta-aminophenols, meta-diphenols, heterocyclic couplers such as, for example, indole derivatives, indoline derivatives, benzimidazole derivatives, benzomorpholine derivatives, sesamol derivatives and pyridine, pyrimidine and pyrazole derivatives, and the acid addition salts thereof.

When present, the oxidation base(s) preferably represent(s) from 0.0005 to 12% by weight approximately relative to the total weight of the dye composition in accordance with the invention, and even more preferably from 0.005 to 8% by weight approximately relative to this weight.

When they are present, the coupler(s) preferably represent(s) from 0.0001 to 10% by weight approximately relative to the total weight of the ready-to-use dye composition, and even more preferably from 0.005 to 8% by weight approximately relative to this weight.

The dye composition according to the invention can also contain one or more direct dyes which can be chosen in particular from azo dyes other than those of the invention, anthraquinones and nitro derivatives of the benzene series, in particular in order to modify the shades or to enrich them with glints.

In general, the acid addition salts which can be used in the context of the dye compositions of the invention (compounds of formulae (I), (II) and (II'), additional oxidation bases and couplers) are chosen in particular from the hydrochlorides, hydrobromides, sulfates, citrates, succinates, tartrates, lactates and acetates.

Another aspect of the invention is a process for dyeing keratin fibers, and in particular human keratin fibers such as the hair using the dye composition as defined above.

According to this process, at least one dye composition as defined above is applied to the fibers for a period which is sufficient to develop the desired colouring, after which the fibers are rinsed, optionally washed with shampoo, rinsed again and dried.

The time required to develop the colouring on the keratin fibers preferably ranges from 3 to 60 minutes and even more precisely from 5 to 40 minutes.

According to one specific embodiment of the invention, and when the dye composition in accordance with the invention contains at least one compound of formula (II) and at least one oxidizing agent, the process includes a preliminary step which comprises separately storing, on the one hand, a composition (A) comprising, in a medium which is suitable for dyeing, at least one compound, such as formula (II) as defined above, and, on the other hand, a composition (B) containing, in a medium which is suitable for dyeing, at least one oxidizing agent, and then in mixing them together at the time of use, before applying this mixture to the keratin fibers.

Another subject of the invention is a multi-compartment dyeing device or "kit" or any other multi-compartment packaging system, a first compartment of which contains composition (A) as defined above and a second compartment of which contains composition (B) as defined above. These devices can be equipped with a means for delivering the desired mixture onto the hair, such as the devices described in patent FR-2,586,913, the disclosure of which is specifically incorporated by reference herein.

The examples which follow are intended to illustrate the invention without, however, limiting its scope.

PREPARATION EXAMPLES

Preparation Example 1

Synthesis of 2-(4-amino)phenyidiazinecarboximidamide hydrochloride 10 g of 2-(4-amino)phenylhydrazinecarboximidamide in 250 ml of methanol were placed in a 500 ml round-bottomed flask at room temperature. 20 g of silver oxide were then added and the mixture was stirred for 30 minutes at room temperature. The reaction mixture was then filtered through a sinter funnel, 10 ml of 5.4 M hydrochloric acid in absolute ethanol were then added and the expected azo compound was then precipitated by adding 1000 ml of diisopropyl ether. By filtration through a sinter funnel and washing with ethyl ether, 7.2 g of 2-(4-amino)phenyidiazinecarboximidamide dihydrochloride, which precipitated in the form of a partially hydrated red solid, were isolated; this compound melted with decomposition at 199° C. and the elemental analysis calculated was:

|  | % | | | |
|---|---|---|---|---|
|  | C | H | N | Cl |
| Calculated | 35.61 | 4.70 | 29.66 | 30.03 |
| Found | 34.11 | 4.93 | 27.46 | 30.72 |

Preparation Example 2

Synthesis of N,N-dimethyl-2-(4-amino)phenyldiazinecarboximidamide hydrochloride

This compound was prepared and purified according to the procedure described above for Example 1.

Starting with 7 g of N,N-dimethyl-2-(4-amino)phenylhydrazinecarboximidamide and 14 g of silveroxide, 4.5 g of 2-(4-amino)phenyldiazinecarboximidamide hydrochloride were isolated in the form of a red solid; this compound melted with decomposition at 246.6° C. and the elemental analysis calculated was:

|  | % | | | |
|---|---|---|---|---|
|  | C | H | N | Cl |
| Calculated | 47.48 | 6.20 | 30.76 | 15.57 |
| Found | 46.17 | 6.32 | 30.04 | 14.08 |

Preparation Example 3

Synthesis of N,N-dimethyl-2-(4-amino)phenylhydrazinecarboximidamide dihydrochloride 4.0 g of N,N-dimethyl-2-(4-nitro)phenylhydrazinecarboximidamide in 100 ml of methanol were placed in a 250 ml reactor. 0.4 g of palladium on charcoal (containing 50% water and 10% active agent) was then introduced. The mixture was hydrogenated for 5 minutes at a pressure of 2 bar, and then filtered through a sinter funnel. The solution was then acidified with 4 ml of hydrochloric ethanol and then precipitated by addition of 400 ml of diisopropyl ether. 3.5 g of N,N-dimethyl-2-(4-amino)phenylhydrazinecarboximidamide dihydrochloride were isolated in the form of a white solid; this compound melted with decomposition at 185.5° C. and the elemental analysis calculated was:

|  | % | | | |
|---|---|---|---|---|
|  | C | H | N | Cl |
| Calculated | 40.61 | 6.44 | 26.31 | 26.18 |
| Found | 39.76 | 6.61 | 25.20 | 26.64 |

Preparation Example 4

Synthesis of 2-(4-amino)phenyl-hydrazinecarboximidamide dihydrochloride 13.8 g of 2-(4-nitro)phenylhydrazinecarboximidamide in 400 ml of a 95/5 methanol/N,N-dimethylformamide mixture were placed in a reactor. 1.4 g of palladium on charcoal (containing 50% water and 10% active agent) were then introduced. The mixture was hydrogenated for 5 minutes at a pressure of 2 bar and was then filtered through a sinter funnel. The solution was then acidified with 15 ml of hydrochloric ethanol and then precipitated by addition of 1000 ml of diisopropyl ether. 6.5 g of 2-(4-amino)phenylhydrazinecarboximidamide dihydrochloride were isolated in the form of a white solid; this compound melted with decomposition at 208° C. and the elemental analysis calculated was:

|  | % | | | |
|---|---|---|---|---|
|  | C | H | N | Cl |
| Calculated | 35.31 | 5.50 | 29.41 | 29.78 |
| Found | 35.03 | 5.71 | 27.85 | 30.40 |

DYEING EXAMPLES

Comparative Examples 1 and 2

The following dye compositions were prepared (contents in grams):

| EXAMPLE | 1(*) | 2 |
|---|---|---|
| 4-Amino-2'-methyl-4'-[N,N-bis(b-hydroxyethyl)amino]phenylazobenzene (compound not forming part of the invention) | 0.472 | — |
| 2-(4-Amino)phenylhydrazinecarboximidamide dihydrochloride (compound of formula (II)) | — | 0.099 |

-continued

| EXAMPLE | 1(*) | 2 |
|---|---|---|
| Common dye support No. 1 | () | () |
| Demineralized water q.s. | 100 g | 100 g |

(*)Example not forming part of the invention
It is important to note that the composition of Example 2 has a molar concentration of dye which is significantly lower than that of Example 1 (i.e. $3.75 \times 10^{-4}$ mol as against $1.5 \times 10^{-4}$ mol).
(**): Common dye support No. 1:

| | |
|---|---|
| Ethylene glycol monoethyl ether | 10 g |
| Cetylstearyl alcohol/sodium lauryl sulfate mixture sold under the name Sinnowax SX$^a$ by Henkel | 2 g |
| Oxyethylenated (3 EO) linear fatty alcohol ($C_{13}$–$C_{15}$) sold under the name Ukanil 25$^a$ by the company PCUK | 3 g |
| Oxyethylenated (7 EO) linear fatty alcohol ($C_{13}$–$C_{15}$) sold under the name Ukanil 43$^a$ by the company PCUK | 2 g |
| Trimethylcetylammonium bromide | 1.5 g |
| Monoethanolamine q.s. | pH 8 |

At the time of use, each of the above dye compositions was applied to locks of natural gray hair containing 90% white hairs, in a proportion of 15 g of composition per 3 g of hair, for 20 minutes. The hair was then rinsed, washed with shampoo, rinsed again and then dried.

The hair dyed with compositions 1 and 2 had the same orange-yellow shade.

In order to determine the increase in colouring more precisely, the color of the locks was evaluated, before and after dyeing, in the Munsell system, using a Minolta CM-2002® colorimeter.

According to the Munsell notation, a color is defined by the expression HV/C in which the three parameters respectively denote the shade or Hue (H), the intensity or Value (V) and the purity or Chromaticity (C), the oblique line in this expression simply being a convention and not indicating a ratio.

The difference between the color of the lock before dyeing and the color of the lock after dyeing expresses the intensity of the colouring and was calculated by applying the Nickerson formula:

$$\Delta E = 0.4 C_0 \Delta H + 6 \Delta V + 3 \Delta C$$

as described, for example, in "Couleur, Industrie et Technique"; pages 14–17; Vol. No. 5; 1978.

In this formula, $\Delta E$ represents the color difference between two locks, $\Delta H$, $\Delta V$ and $\Delta C$ represent the variation in absolute values of the parameters H, V and C, and $C_0$ represents the purity of the lock with respect to which it is desired to evaluate the color difference.

The greater the value of $\Delta E$, the more intense the colouring.

The results are given in the table below:

| COMPOSITION | Color of the hair before dyeing | Color of the hair after dyeing | Intensity of the colouring | | | |
|---|---|---|---|---|---|---|
| | | | $\Delta H$ | $\Delta V$ | $\Delta C$ | $\Delta E$ |
| 1(*) | 3.05 Y 5.7/1.9 | 1.85 Y 5.2/5.4 | 1.2 | 0.5 | 3.5 | 14.4 |

-continued

| COMPOSITION | Color of the hair before dyeing | Color of the hair after dyeing | Intensity of the colouring | | | |
|---|---|---|---|---|---|---|
| | | | $\Delta H$ | $\Delta V$ | $\Delta C$ | $\Delta E$ |
| 2 | 3.05 Y 5.7/1.9 | 1.58 Y 5.3/5.2 | 1.5 | 0.4 | 3.3 | 13.4 |

(*)Example not forming part of the invention.

These results show that Composition 2 in accordance with the invention gives a colouring which is essentially as intense as that of composition 1, which does not form part of the invention and which contains a dye which does not form part of the invention, at a molar concentration which is significantly larger than that used in Composition 2.

Examples 3 to 6 of Direct Dyeing

The following dye compositions were prepared (contents in grams):

| EXAMPLE | 3 | 4 | 5 | 6 |
|---|---|---|---|---|
| 2-(4-Amino)phenylhydrazinecarboximidamide dihydrochloride (compound of formula (II)) | 0.396 | 0.099 | — | — |
| N,N-Dimethyl-2-(4-amino)phenylhydrazinecarboximidamide dihydrochloride (compound of formula (II)) | — | — | 0.399 | — |
| N,N-Dimethyl-2-(4-amino)phenyl-diazinecarboximidamide dihydrochloride (compound of formula (I)) | — | — | — | 0.396 |
| Common dye support No. 1 | () | () | () | () |
| Demineralized water q.s. | 100 g | 100 g | 100 g | 100 g |

(**): Common dye support No. 1:
This is identical to the one used above for Examples 1 and 2.

Locks of natural gray hair containing 90% white hairs were dyed with each of the above compositions according to the dyeing process described above for Examples 1 and 2.

The shades obtained are given in the table below:

| EXAMPLE | SHADE OBTAINED |
|---|---|
| 3 | Coppery orange |
| 4 | Yellow-orange |
| 5 | Yellow-orange |
| 6 | Red-orange |

Examples 7 to 15 of Oxidation Dyeing

The following dye compositions were prepared (contents in grams):

| | EXAMPLE | | | | | | | | |
|---|---|---|---|---|---|---|---|---|---|
| | 7 | 8 | 9 | 10 | 11 | 12 | 13 | 14 | 15 |
| 2-(4-Amino)phenylhydrazinecarboximidamide dihydrochloride (compound of formula (II)) | 0.74 | 0.74 | 0.74 | 0.74 | 0.74 | 0.74 | 0.74 | 0.74 | — |
| N,N-Dimethyl-2-(4-amino)phenyl-hydrazinecarboximidamide dihydrochloride (compound of formula (II)) | — | — | — | — | — | — | — | — | 0.199 |
| para-Phenylenediamine (oxidation base) | — | — | — | — | — | 0.324 | 0.324 | — | — |
| para-Aminophenol (oxidation base) | — | — | — | — | — | — | — | 0.327 | — |
| 2,4-Diaminophenoxyethanol dihydrochloride (coupler) | — | 0.723 | — | — | — | 0.723 | — | — | — |
| 2-Methyl-5-N-(b-hydroxyethyl)aminophenol (coupler) | — | — | 0.504 | — | — | — | — | — | — |
| meta-Aminophenol (coupler) | — | — | — | 0.327 | — | — | — | 0.327 | — |
| Resorcinol (coupler) | — | — | — | — | 0.33 | — | 0.33 | — | — |
| Common dye support No. 2 | (*) | (*) | (*) | (*) | (*) | (*) | (*) | (*) | (***) |
| Demineralized water q.s. | 100 g | 100 g | 100 g | 100 g | 100 g | 100 g | 100 g | 100 g | 100 g |

(**): Common dye support No. 2:
| | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name Ethomeen O12 ® by the company Akzo | 7.0 g |
| Diethylaminopropyl laurylaminosuccinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulfite as an aqueous solution containing 35% A.M. | 0.455 g A.M. |
| Ammonium acetate | 0.8 g |
| Antioxidant, sequestering agent | q.s. |
| Fragrance, preserving agent | q.s. |
| Aqueous ammonia containing 20% NH$_3$ | 10.0 g |

At the time of use, each of the above dye compositions was mixed, weight for weight, with a 20-volumes hydrogen peroxide solution (6% by weight) of pH 3.

The mixture obtained was applied to locks of natural or permanent-waved gray hair containing 90% white hairs, for 30 minutes. The locks were then rinsed, washed with a standard shampoo, rinsed again and then dried.

The shades obtained are given in the table below:

| EXAMPLE | SHADE OBTAINED |
|---|---|
| 7 | Yellow-orange |
| 8 | Orange-brown |
| 9 | Orange |
| 10 | Red-orange |
| 11 | Yellow-orange |
| 12 | Black-brown |
| 13 | Brown-orange |
| 14 | Yellow-orange |
| 15 | Orange-yellow |

What is claimed is:

1. An azo compound of formula (I) or the acid addition salt thereof:

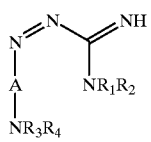

(I)

in which:
R$_1$ and R$_2$, independently of each other, represent a hydrogen atom; a C$_1$–C$_6$ alkyl radical; a 5- or 6-membered cycloalkyl radical; a 5- or 6-membered aromatic ring; a 5- or 6-membered aromatic ring substituted with a C$_1$–C$_6$ alkyl radical, a halogen atom, an amino radical, a hydroxyl radical, or a C$_1$–C$_6$ alkoxy radical; or R$_1$ and R$_2$ form, together with the nitrogen atom to which they are attached, a 4- to 8-membered heterocycle, said heterocycle containing one or more hetero atoms chosen from sulfur, nitrogen and oxygen;

R$_3$ and R$_4$, independently of each other, represent a hydrogen atom, a C$_1$–C$_6$ alkyl radical, a C$_1$–C$_6$ monohydroxyalkyl radical or a C$_2$–C$_6$ polyhydroxyalkyl radical; and A is a 5- to 6-membered aromatic ring which can be interrupted by one or more hetero atoms chosen from sulfur, nitrogen and oxygen, or fused to another 5- to 6-membered aromatic ring.

2. The compound of claim 1 or salt thereof, wherein the $C_1$–$C_6$ alkyl radicals are chosen from methyl, ethyl, n-propyl, isopropyl, n-butyl, isobutyl, tert-butyl, n-pentyl, isopentyl, n-hexyl, and isohexyl radicals.

3. The compound of claim 1 or salt thereof, wherein the $C_1$–$C_6$ monohydroxyalkyl radical is chosen from hydroxymethyl, hydroxyethyl, hydroxypropyl, and hydroxybutyl radicals.

4. The compound of claim 1 or salt thereof, wherein the $C_2$–$C_6$ polyhydroxyalkyl radical is chosen from dihydroxyethyl, dihydroxypropyl, trihydroxypropyl, and dihydroxybutyl radicals.

5. The compound of claim 1 or salt thereof, wherein the cycloalkyl radical is chosen from cyclohexyl and cyclopentyl.

6. The compound of claim 1 or salt thereof, wherein the aromatic rings are chosen from phenyl rings; phenyl rings substituted with a $C_1$–$C_6$ alkyl radical, a halogen atom, an amino radical, a hydroxyl radical, or a $C_1$–$C_6$ alkoxy radical; benzyl, pyrimidine, pyridazine, and benzimidazole rings.

7. The compound of claim 1 or salt thereof, wherein said 4- to 8-membered heterocycle is chosen from imidazole, benzotriazole, benzimidazole, pyrrolidine, piperidine, and morpholine rings.

8. The compound of claim 1 or salt thereof, wherein the aromatic ring A is a 6-membered ring chosen from phenyl, pyrimidine and pyridine rings, or a 5-membered ring chosen from pyrrole and pyrazole rings.

9. The compound of claim 1, wherein the compound or salt thereof is chosen from:

2-(4-amino)phenyldiazinecarboximidamide,
N,N-dimethyl-2-(4-amino)phenyldiazinecarboximidamide,
N,N-diethyl-2-(4-amino)phenyldiazinecarboximidamide,
N,N-diisopropyl-2-(4-amino)phenyldiazinecarboximidamide,
N,N-dibutyl-2-(4-amino)phenyidiazinecarboximidamide,
2-(5-amino)-2-pyridyldiazinecarboximidamide, and the acid addition salts thereof.

10. A method for making a compound of formula (I) or the acid addition salt thereof comprising the steps of:

(a) carrying out a reduction reaction in a solvent medium on a compound of formula (III) below

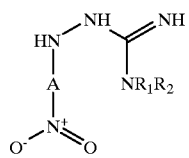

(III)

in which $R_1$ and $R_2$, independently of each other, represent a hydrogen atom; a $C_1$–$C_6$ alkyl radical; a 5- or 6-membered cycloalkyl radical; a 5- or 6-membered aromatic ring; a 5- or 6-membered aromatic ring substituted with a $C_1$–$C_6$ alkyl radical, a halogen atom, an amino radical, a hydroxyl radical, or a $C_1$–$C_6$ alkoxy radical; or $R_1$ and $R_2$ form, together with the nitrogen atom to which they are attached, a 4- to 8-membered heterocycle, said heterocycle containing one or more hetero atoms chosen from sulfur, nitrogen and oxygen;

A is a 5- to 6-membered aromatic ring which can be interrupted by one or more hetero atoms chosen from sulfur, nitrogen and oxygen, or fused to another 5- to 6-membered aromatic ring; for a time sufficient to give a compound of formula (II) or the acid addition salt thereof:

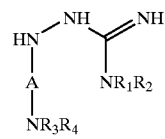

(II)

in which:

$R_1$ and $R_2$, independently of each other, represent a hydrogen atom; a $C_1$–$C_6$ alkyl radical; a 5- or 6-membered cycloalkyl radical; a 5- or 6-membered aromatic ring; a 5- or 6-membered aromatic ring substituted with a $C_1$–$C_6$ alkyl radical, a halogen atom, an amino radical, a hydroxyl radical, or a $C_1$–$C_6$ alkoxy radical; or $R_1$ and $R_2$ form, together with the nitrogen atom to which they are attached, a 4- to 8-membered heterocycle, said heterocycle containing one or more hetero atoms chosen from sulfur, nitrogen and oxygen;

$R_3$ and $R_4$, independently of each other, represent a hydrogen atom, a $C_1$–$C_6$ alkyl radical, a $C_1$–$C_6$ monohydroxyalkyl radical or a $C_2$–$C_5$ polyhydroxyalkyl radical; and A is a 5- to 6-membered aromatic ring which can be interrupted by one or more hetero atoms chosen from sulfur, nitrogen and oxygen, or fused to another 5- to 6-membered aromatic ring; and (b) oxidizing the compound of formula (II) in a solvent for a time sufficient to give the compound of formula (I) or an acid addition salt thereof:

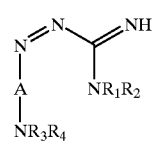

(I)

in which:

$R_1$ and $R_2$, independently of each other, represent a hydrogen atom; a $C_1$–$C_6$ alkyl radical; a 5- or 6-membered cycloalkyl radical; a 5- or 6-membered aromatic ring; a 5- or 6-membered aromatic ring substituted with a $C_1$–$C_6$ alkyl radical, a halogen atom, an amino radical, a hydroxyl radical, or a $C_1$–$C_6$ alkoxy radical; or $R_1$ and $R_2$ form, together with the nitrogen atom to which they are attached, a 4- to 8-membered heterocycle, said heterocycle containing one or more hetero atoms chosen from sulfur, nitrogen and oxygen;

$R_3$ and $R_4$, independently of each other, represent a hydrogen atom, a $C_1$–$C_6$ alkyl radical, a $C_1$–$C_6$ monohydroxyalkyl radical or a $C_2$–$C_6$ polyhydroxyalkyl radical; and A is a 5- to 6-membered aromatic ring which can be interrupted by one or more hetero atoms chosen from sulfur, nitrogen and oxygen, or fused to another 5- to 6-membered aromatic ring.

* * * * *